(12) United States Patent
Grier

(10) Patent No.: US 7,586,684 B2
(45) Date of Patent: Sep. 8, 2009

(54) SOLUTE CHARACTERIZATION BY OPTOELECTRONKINETIC POTENTIOMETRY IN AN INCLINED ARRAY OF OPTICAL TRAPS

(75) Inventor: David G. Grier, New York, NY (US)

(73) Assignee: New York University, New York, NY (US)

( * ) Notice: Subject to any disclaimer, the term of this patent is extended or adjusted under 35 U.S.C. 154(b) by 255 days.

(21) Appl. No.: 11/040,665

(22) Filed: Jan. 21, 2005

(65) Prior Publication Data

US 2006/0163463 A1    Jul. 27, 2006

(51) Int. Cl.
G02B 27/44 (2006.01)
G01N 33/543 (2006.01)
C12N 13/00 (2006.01)

(52) U.S. Cl. .................... 359/566; 436/518; 435/173.1
(58) Field of Classification Search .............. 435/6, 435/7.1, 173.1; 250/251, 291; 359/566; 436/518

See application file for complete search history.

(56) References Cited

U.S. PATENT DOCUMENTS

| 3,763,428 | A  | * | 10/1973 | Preist ..................... 324/71.1 |
| 6,797,942 | B2 | * | 9/2004  | Grier et al. ................. 250/251 |
| 6,815,664 | B2 |   | 11/2004 | Wang et al. |
| 6,842,285 | B2 |   | 1/2005  | Gluckstad |
| 6,991,906 | B1 | * | 1/2006  | Fuhr et al. .................... 435/7.1 |
| 7,118,676 | B2 | * | 10/2006 | Mueth et al. ................. 210/732 |
| 7,201,833 | B2 | * | 4/2007  | Lauks et al. ................. 204/600 |
| 7,309,992 | B2 | * | 12/2007 | Kudryavtsev et al. ....... 324/464 |
| 2002/0122254 | A1 | | 9/2002 | Gluckstad |
| 2003/0007894 | A1 | | 1/2003 | Wang et al. |
| 2004/0258353 | A1 | | 12/2004 | Gluckstad et al. |
| 2005/0094232 | A1 | | 5/2005 | Kibar |
| 2005/0164372 | A1 | | 7/2005 | Kibar |

FOREIGN PATENT DOCUMENTS

WO    WO 2004/012133 A2    2/2004

* cited by examiner

Primary Examiner—Audrey Y Chang
(74) Attorney, Agent, or Firm—Foley & Lardner LLP

(57) ABSTRACT

A method and apparatus for selecting a specific fraction from a heterogeneous fluid-borne sample using optical gradient forces in a microfluidic or fluidic system are presented. Samples may range in size from a few nanometers to at least tens of micrometers, may be dispersed in any fluid medium, and may be sorted on the basis of size, shape, optical characteristics, charge, and other physical properties. The selection process involves passive transport through optical intensity field driven by flowing fluid, and so offers several advantages over competing techniques. These include continuous rather than batch-mode operation, continuous and dynamic tunability, operation over a wide range of samples, compactness, and low cost.

13 Claims, 7 Drawing Sheets

US 7,586,684 B2

SOLUTE CHARACTERIZATION BY OPTOELECTRONKINETIC POTENTIOMETRY IN AN INCLINED ARRAY OF OPTICAL TRAPS

The present invention was supported by the National Science Foundation under Grant Number DBI-0233971, with additional support from Grant Number DMR-0304906.

FIELD OF THE INVENTION

The present invention relates to modulated optical tweezers. More particularly, the present invention relates to the use of modulated optical tweezers in a variety of situations.

BACKGROUND OF THE INVENTION

Since their introduction a decade ago, optical tweezers have become indispensable tools for physical studies of macromolecular and biological systems. Formed by bringing a single laser beam to a tight focus, an optical tweezer exploits optical gradient forces to manipulate micrometer-sized objects. Optical tweezers have allowed scientists to probe the small forces that characterize the interactions of colloids, polymers and membranes, and to assemble small numbers of colloidal particles into mesoscopic structures. Conventional efforts each required only one or two optical tweezers. Extending these techniques to larger and more complex systems requires larger and more complex arrays of optical traps.

Related techniques for creating multiple simultaneous optical traps include the generalized phase contrast method, interferometric optical tweezers, and optical lattices. The latter two approaches involve interfering multiple beams in the volume of the sample, while the former might be considered a variant of holographic optical trapping. Interferometric techniques can cover larger areas than holographic techniques, but are substantially more limited in the types of intensity patterns that can be created. In particular, interferometric optical tweezers and optical lattices are limited to periodic structures.

A single laser beam brought to a focus with a strongly converging lens forms a type of optical trap widely known as an optical tweezer. In general, such a beam can be described by a wave function, $$\psi(r) = A(r) \exp(i\phi(r)) \quad (1)$$

where $A(r)$ is the amplitude profile and $\phi(r)$ is the phase at position r in a plane transverse to the optical axis.

A conventional optical tweezer is created from the $TEM_{00}$ laser beam provided by a typical laser. Such a beam's wave fronts are planar and can be described by the uniform phase profile $\phi(r) = \phi 0$. Bringing such a beam to a diffraction-limited focus with an appropriate focusing element, such as a microscope objective lens, transforms the beam into an optical tweezer. The position of the optical tweezer in the lens' focal plane is determined by the angle at which the team enters the lens' input pupil. Additionally, if the beam is diverging as it enters the input pupil, it comes to a focus and forms an optical tweezer downstream of the focal plane. Alternatively, if the beam is converging, it forms a trap upstream of the focal plane.

Multiple beams of light passing simultaneously through the lens input pupil yield multiple optical tweezers, each at a location determined by the angle of incidence arid degree of collimation at the input pupil. These beams form an interference pattern as they pass through the input pupil, whose amplitude and phase corrugations characterize the downstream trapping pattern. Imposing the same modulations on a single incident beam at the input pupil would yield the same pattern of traps, but without the need to create and direct a number of independent input beams. Such wave front modification can be performed by a type of diffractive optical element (DOE) commonly known as a hologram. Generally, the hologram or DOE encoding a particular pattern of optical traps can be calculated with a computer through a procedure known as computer-generated holography (CGH). Using CGH to create arbitrary configurations of multiple optical traps constitutes a new class of optical micromanipulation tools known as holographic optical tweezers (HOT), with manifold applications in the physical and biological sciences as well as in industry.

The efficacy of holographic optical tweezers is determined by the quality of the trap-forming DOE, which in turn reflects the performance of the numerical algorithms used in their computation. Previous studies have applied holograms calculated by simple linear superposition of the input fields or with variations on the classic Gerchberg-Saxton and Adaptive-Additive algorithms. Despite their general efficacy, these algorithms yield traps whose relative intensities can differ substantially from their design values, and typically result in undesirable "ghost" traps. These problems can become acute for complicated three dimensional trapping patterns, particularly when the same hologram also is used as a mode converter to project multifunctional arrays of optical traps.

The holograms used for holographic optical trapping typically operate only on the phase of the incident beam, and not its amplitude. Such phase-only holograms, also known as kinoforms, are far more efficient than amplitude-modulating holograms, which necessarily divert light away from the beam. They also are substantially easier to implement than fully complex holograms that would be required to create arbitrary superpositions at the input pupil. Indeed, sequences of kinoforms can be projected with a computer-addressed spatial light modulator (SLM) to create dynamic holographic optical tweezers.

General trapping patterns can still be achieved with kinoforms despite the loss of information that might be encoded in amplitude modulations because optical tweezers rely for their operation on intensity gradients and not local phase variations. However, it is still necessary to find a. pattern of phase shifts in the input plane that encodes the desired intensity pattern in the focal volume.

SUMMARY OF THE INVENTION

The present invention relates a variant of optical tweezers in which the trap's stiffness is made to vary with direction. In particular, the modified trap's intensity spreads more broadly in selected directions, thereby reducing its stiffness in those directions, or facilitating alignment of asymmetric objects along those directions. Such modified traps may be used to facilitate objects' escape along selected directions and to orient and rotate non-compact objects. The ability to facilitate objects' escape along selected directions has applications for optical fractionation, in which objects' differing interactions with optical traps are used as the basis for sorting. The ability to orient and rotate non-compact objects may be used in assembling micrometer-scale objects.

Previously reported methods for orienting objects in optical traps include creating optical tweezers from Gauss-Hermite modes, modifying their amplitude profiles with rectangular apertures, rotating the polarization angle of linearly and elliptically polarized light, interfering Laguerre-Gaussian modes with plane waves to create symmetric spiral patterns, modulating normally circular optical vortices and projecting multiple conventional optical tweezers in close proximity.

The present invention also relates to a new class of algorithms for HOT CGH calculation based on direct search and simulated annealing that take advantage of recently introduced metrics to achieve unprecedented trap-formation accuracy and optical efficiency.

The present invention is preferably implemented through holographic optical trapping, but also can be implemented with other related techniques such as the generalized phase contrast method, interferometric optical tweezers, and optical lattices.

One implementation of the invention is an apparatus for selecting fractions through optical fractionation that includes at least two channels for providing at least first and second laminar fluid flows, respectively. At least one of the two fluid flows contains fluid-borne particles. A holographic optical tweezer system projects at least two optical arrays of optical traps onto a region at a junction of at least the two channels. The two arrays of optical traps each selectively deflect the fluid-borne particles for fractionating the fluid-borne particles according to a characteristic of the fluid-borne particles.

Another implementation of the invention is an apparatus for selecting fractions through optical fractionation, including N channels for providing N laminar input streams. At least one of the N laminar input streams contains fluid-borne particles. A holographic optical tweezer system projects an optical array on a region of a junction of the channels to fractionate the fluid-borne particles in the N laminar input streams into M laminar output streams, where N does not necessarily equal M.

The present invention also relates to methods for creating holographic optical traps with two separate input lasers, with applications including creating holographic optical traps (HOTs) with two wavelengths of light. These methods can be extended to include more than two input lasers.

In addition, the present invention describes a method for characterizing several aspects of a solute's charge state, size, size polydispersity, and other properties as it is driven by flowing solvent through an array of optical traps inclined with respect to the flow direction.

These and other objects, advantages and features of the invention, together with the organization and manner of operation thereof, will become apparent from the following detailed description when taken in conjunction with the accompanying drawings, wherein like elements have like numerals throughout the several drawings described below.

DETAILED DESCRIPTION OF THE PREFERRED EMBODIMENTS

Figure 1:
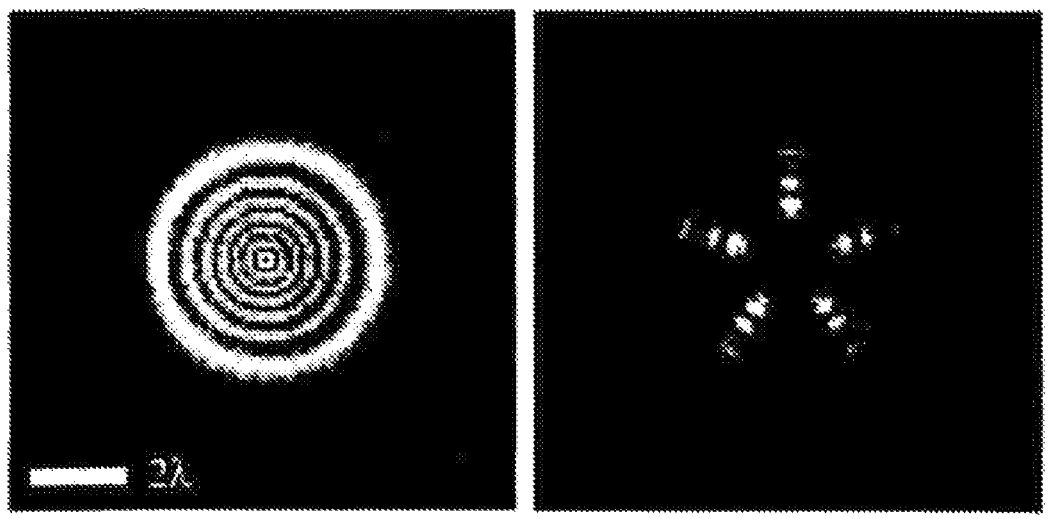
FIG. 1 shows modulated optical tweezer, wherein the left panel shows the unmodulated intensity profile of a conventional optical tweezer created from a beam with a flat-top profile at a distance $z=5\lambda$ from the focus, where $\lambda$ is the wavelength of light, and wherein the right panel shows an equivalent cross-section through a beam sinusoidally modulated according to $\phi(\vec{r})=\alpha_m \sin(m\theta-\theta_m)$ with $m=5$, $\alpha_m=1$, and $\theta_m=0$.

Optical traps refer to a type of force exerted by a beam of light to trap and move small objects. In general, these forces fall into two categories: (1) radiation pressure that tends to push objects down the axis of a beam, and (2) optical gradient forces. Optical gradient forces arise because objects develop electromagnetic dipole moments when illuminated by light. Intensity gradients in the light exert forces on these dipole moments whose sign depends on the relative dielectric constants of the object and the surrounding medium. Particles with higher dielectric constants than their surroundings (high-dielectric particles) generally are drawn up by the gradients toward brighter regions while low-dielectric particles are pushed away to darker regions.

Optical gradient forces provide the basic forces necessary for the single-beam optical trap known as an optical tweezer. An optical tweezer comprises a single beam of light brought to a diffraction-limited focus by a high-numerical aperture lens, such as a microscope objective lens. High-dielectric objects are drawn toward the focal point, where the light is most intense. At the same time, they are repelled by radiation pressure that tends to drive them downstream. If the gradient forces dominate, the particles can be stably trapped somewhere near the focal point.

In other words, the focused beam of light provides a three-dimensional potential energy well for high-dielectric particles, and a potential energy barrier for particles that are repelled by the light. The latter class of particles repelled by radiation pressure includes low-dielectric particles, as well as particles that strongly absorb or reflect the focused light. All of these effects can be enhanced and modified if the wavelength of light is near a resonance of the particle.

A single beam of light brought to a single focus creates a single optical tweezer, and therefore, a single localized potential well. The holographic optical tweezer technique creates multiple simultaneous independent optical tweezer from a single beam of light and a single focusing element. Consequently, holographic optical tweezers can create any desired three dimensional arrangement of potential energy wells or barriers.

Creating multiple holographic optical traps applies the same basic optical principles used to create a single optical tweezer. In particular, a collimated beam of light coaxial with the optical axis of a focusing element, such as an infinity-corrected objective lens, is brought to a focus in the middle of the focusing element's focal plane, and forms a trap accordingly. A collimated beam entering the focusing element's entrance pupil at an angle comes to a focus in the focal plane, but at a point displaced from the optical axis by an amount that depends on the angle of incidence and in a direction that depends on the direction of the tilt. Changing the angle of incidence therefore changes the location of the resulting trap in the focal plane of the focusing element, and allows the trap to be translated in two dimensions. Changing the beam's degree of collimation moves the trap in the third dimension, along the optical axis. A slightly diverging beam passing through the entrance pupil comes to a focus downstream of the focal plane, while a slightly converging beam comes to a focus upstream. The axial displacement of the focal point depends on the degree of collimation. Controlling both the angle of incidence and degree of collimation of the beam as it passes through the focusing element's entrance pupil therefore controls the position of the resulting optical tweezer in three dimensions, with a single input beam resulting in a single trap.

Several beams of light all passing through the focusing element's entrance pupil at different angles and with different degrees of collimation would form multiple optical traps at different positions in the focusing element's focal volume. If all of the beams have the same wavelength, they could be derived from the same source. Creating multiple simultaneous traps, therefore, requires a method for creating multiple beams all propagating in particular directions, each with its own specific degree of collimation, and all passing through the entrance pupil of the focusing element. Holographic optical trapping solves this problem in a very general way, as described in U.S. Pat. Nos. 6,055,106; 6,416,190; 6,624,940; 6,626,546; and 6,639,208, all of which are incorporated herein by reference.

Multiple coherent beams of light passing through the plane of the entrance pupil form an interference pattern composed of spatial variations in light amplitude and phase. A single beam of light imprinted with the same variations would propagate in the same way as the multiple beams—this is the principle of holography. A device that imprints the particular modulation required to transform a single beam into a desired fan-out of beams may be said to project the associated hologram. More specifically, a device commonly known as a diffractive beam splitter, a holographic beam splitter, or a kinoform constitutes an example of a diffractive optical element (DOE) that can be used to create holographic optical traps.

Placing the appropriate hologram in the entrance pupil of the focusing element, or in a plane conjugate to the entrance pupil, transforms a single input beam of light into many beams, all passing through the focusing element's entrance pupil. Each beam can have a specified angle of incidence and a specified degree of collimation. Consequently, each forms an independent trap in the focal volume.

The resulting pattern of traps is specified by the hologram. The hologram, in turn, can be implemented in many ways. Most preferably, the holograms can be designed by computers to create specific patterns of traps.

This design process must take into consideration factors such as the amplitude profile of the input beam. Modulating the amplitude of a beam of light generally involves diverting energy out of the beam, either by absorption or by reflection. In the former case, the absorbed light will tend to heat the absorber, limiting the amount of power that can be used to create the traps. In either case, the diverted light reduces the efficiency by which a single beam of light can be used to create multiple traps, each of which requires a certain intensity to operate as desired. In many cases, a desired pattern of optical traps can be created by modulating only the phase profile of the input beam, and not its amplitude profile. This flexibility is available because optical trapping relies on the intensity of the trapping light, and thus on the amplitude, but not on the phase. As a result, infinitely many different patterns of phase modulation at the input plane of the focusing lens yield the same intensity distribution in the output plane for a given amplitude profile. Consequently, a phase modulation can be chosen to create the desired pattern of traps without diverting energy from the beam. The resulting phase-only DOE can be implemented through variations in the thickness of a transparent medium such as glass, through the surface relief of a mirror, or by controlling the index of refraction of a medium such as a liquid crystal layer through which the light passes.

A computer-designed phase-only DOE can be implemented with a device or medium whose relevant optical properties can be deliberately changed so that the hologram it encodes can be updated accordingly. Such a dynamic implementation of a trap-forming DOE can be used to update the beam pattern in real time so that the resulting trapping pattern can be changed. This transforms conventional holographic optical traps into dynamic holographic optical traps.

Holographic optical tweezers can project any desired pattern of potential wells or barriers into a transparent medium. This capability can be combined with properties of fluids flowing at low Reynolds numbers to create a method for sorting fluid-borne objects. This sorting by light is referred to as optical fractionation. The basic optical fractionation technique is based on holographic optical trapping and is disclosed in published U.S. Patent Application 2003/0047676, which is incorporated herein by reference.

Fluids flowing at low Reynolds numbers undergo smooth laminar flow and therefore undergo no mixing. Such flows can be achieved by reducing the dimensions of a channel through which the fluid passes, by reducing the flow speed, or by some combination of approaches. The field of microfluidics is based on this principle. Consider two laminar streams coming together at a junction-between two channels. If the resulting flow still maintains a low enough Reynolds number, the two streams cannot mix, but rather flow side-by-side separately, even if they consist of the same fluid. Eventually two miscible streams will mix through interdiffusion, but this can require a substantial interval. Before this happens, the two streams can be separated again into separate channels. A set of channels that brings two streams together, allows them to flow together for a period and then separates them again is known as an H-junction.

H-junctions are useful for sorting fluid-borne objects. An object carried along in one of the streams generally will continue in that stream and come out the other side of the junction still in its stream. However, if the object diffuses or otherwise makes its way across the interface between the two flows, then it will be collected in the other stream at the output of the H-junction. Consider two streams entering an H-junction, one containing a heterogeneous sample and the other containing an empty buffer fluid. Any object crossing the H-junction's interface will be carried away by the buffer, and can be collected. If some of the objects in the mixture are more diffusive than others, the more diffusive objects will cross the interface preferentially and will be collected with higher efficiency than the others. Similarly, the initial flow will be relatively enriched in the less-diffusive fraction upon exiting the H-junction.

This approach has at least three shortcomings. Macromolecular samples diffuse relatively slowly, so that effective separations require H-junctions with substantial interfacial areas. Furthermore, the most diffusive fraction can do no better than spread throughout the buffer and sample flows. This limits the ultimate separation efficiency for a single pass through an H-Junction. Finally, an object's diffusion coefficients tend to depend only linearly on their size, so that fractionation in H-junctions is unlikely to offer the resolution required to separate fractions that differ only slightly from each other. Optical fractionation overcomes these deficiencies while adding a spectrum of other advantages.

When a fluid-borne object encounters an array of optical traps, the traps can act as potential energy wells. When the maximum trapping force is comparable to the maximum driving force, objects interact strongly with the traps but do not end up localized in them. Under these circumstances, the flowing particle's trajectory can be deflected enough by its encounter with one trap that it falls into the domain of influence of the next trap in the array. If the traps in the array are evenly spaced, and if the array is not aligned with the driving force, then the particle's trajectory can be systematically deflected away from the driving force's direction. The particle then selects a direction that is commensurate with a symmetric direction through the array, but not aligned with the driving force. Such a trajectory is said to be locked in to the array.

Different objects interact differently with the same pattern of optical traps, so that the potential energy landscape that a given object experiences in an array of traps depends on its properties. Consequently, different objects with different properties driven by the same force through the same array of optical traps need not follow the same trajectory. In particular, one type of object can become locked in to the array under the same conditions that another type of object can escape. The locked-in class therefore is systematically deflected by the array, while the other is not.

In the situation where the array of traps is placed across the sample flow in a microfluidic H-junction, those objects that become locked in to the array are deflected across the interface between the two flows and can be collected in the buffer. Objects that escape the array will be retained by the sample stream.

At a minimum, the modulated potential energy landscape provides a mechanism to tune the transfer of fluid borne objects across the interface of an H-junction and thereby provides a degree of optimization not otherwise available. Moreover, a distinction between locked-in and free states can depend with exponential sensitivity on an object's size, and thus this distinction qualitatively surpasses the sensitivity offered by diffusion alone. Furthermore, because optical fractionation can be accomplished over the extent of a small array of traps, long H-junctions are not required.

Which fraction is deflected by an array of optical tweezers is determined by the separation between traps, the symmetry of the array, the intensity of the traps, the angle of inclination, and the wavelength of light used. All of these characteristics can be changed dynamically to optimize the selection for a particular fraction. These also are advantages, therefore, over separation by diffusion alone. Furthermore, optical trapping has been demonstrated for objects as small as 5 nanometers and as large as several hundred micrometers. Thus, optical fractionation is useful over this entire size range. The same physical apparatus, moreover, can be used over the entire range. This is a substantial advantage over all other known sorting techniques. Finally, arrays can be designed so that every object satisfying the lock-in criterion is deflected across the interface. Nearly perfect sorting can therefore be achieved with a single line of traps inclined with respect to the flow, spanning the sample stream and extending slightly into the buffer stream.

Figure 4:
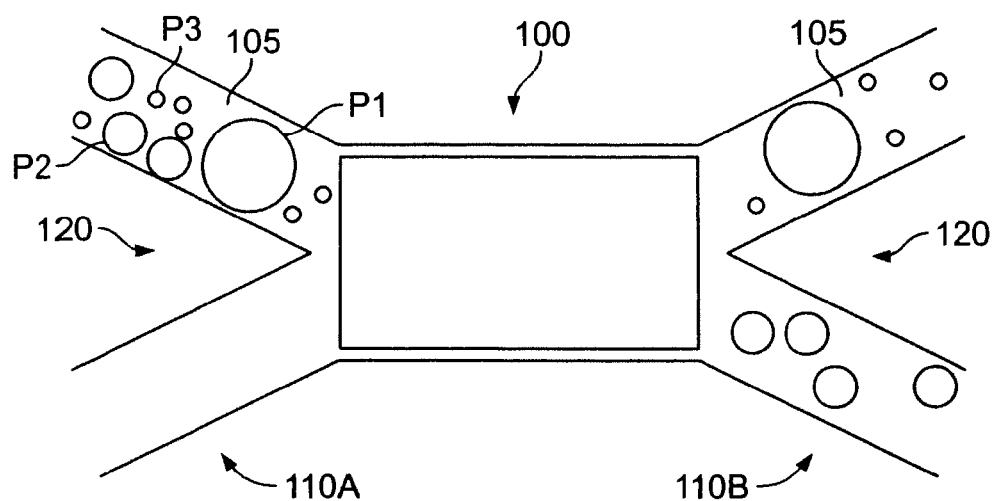
FIG. 4 shows an H-junction having a plurality of laminar input streams coming together into a single interaction region and then separating into a plurality of output streams.

Although the following discussion focuses on fractionation by size, the same principles may also be applied to sorting on the basis of other properties as well. The fraction selected by a particular array includes all objects of a certain size and above. In many applications, only a particular size range might be required. Or, conversely, it might be necessary to remove a particular size range from a sample, for instance, to create a bimodal distribution. This could be implemented with two passes through single-stage optical fractionation systems, one to remove the fraction that is too large, and the other to pick off the desired fraction. However, these two steps can be combined through the use of a single appropriately designed array of traps projected into a single H-junction as shown in FIG. 4. This is referred to as multi-stage or multi-functional optical fractionation. Several variants of this approach will be described below, as is a basic method for selecting multiple fractions simultaneously.

FIG. 4 shows a first variant of the basic method in which particles of types P1, P2 and P3 are carried by a sample stream 105 into an H-junction 100. When the flow passes through a first manifold of optical traps 110A, all particles of a particular size and larger, for example, P1 and P2, are swept into the buffer stream 120. If the buffer stream 120 now encounters a second array of traps 110B designed to deflect some of the first fraction, for example, P1, back into the sample stream, then the remaining fraction in the buffer stream includes only particles of a particular specified size range, P2. The second array of traps can be projected with the same DOE that created the initial array, and thus can use the same laser. More generally, the second array can be created with a second DOE that also is conjugate to the focusing element's entrance pupil, with a single DOE specially designed to create two distinct trapping patterns from the two different wavelengths of light.

The net effect is that two distinct optical trap arrays 110A and 110B are projected into the same H-junction 100 such that the first sweeps both the desired fraction and another undesired fraction across the interface and the second sweeps the undesired fraction back into the initial sample stream. The result is that the buffer stream 120 exiting the H-junction contains only the selected fraction P2, and the sample stream contains everything else, P1 and P3.

Figure 5:
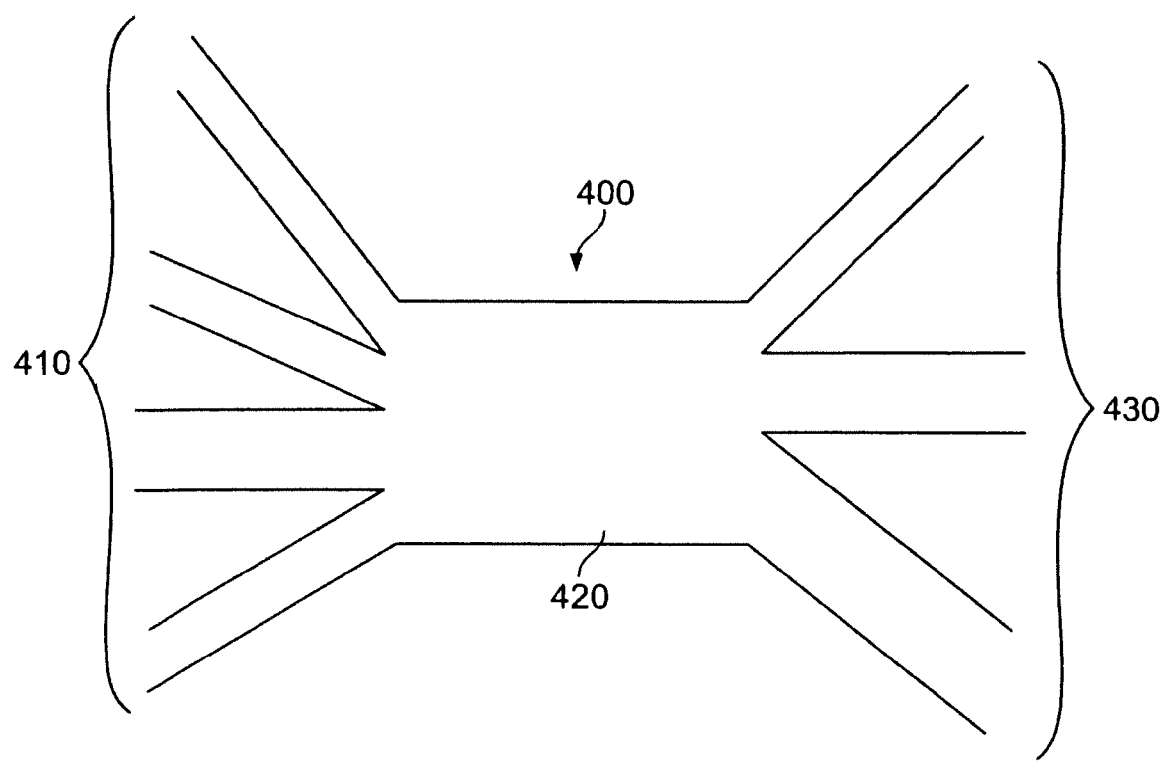
FIG. 5 shows an embodiment of the present invention in which a single input sample is dispersed into several discrete fractions.

An H-junction 400 can be generalized to include a number N of laminar input streams 410 coming together into a single interaction region 420 and then separating into M output streams 430, as shown in FIG. 5. In general, N does not have to equal M. A single pattern of optical traps spanning the multi-stream interaction region 420 and taking the form of multiple arrays, therefore, can transfer fractions of an initial sample distributed in any of the input streams into any of the output streams. The optical intensity pattern in this case may be thought of as a switching yard, shuttling in-flowing objects into desired outgoing streams. Because the pattern of traps can be changed by updating the trap-forming DOE(s), which fraction finds its way to which output stream can be altered and optimized dynamically.

Figure 6:
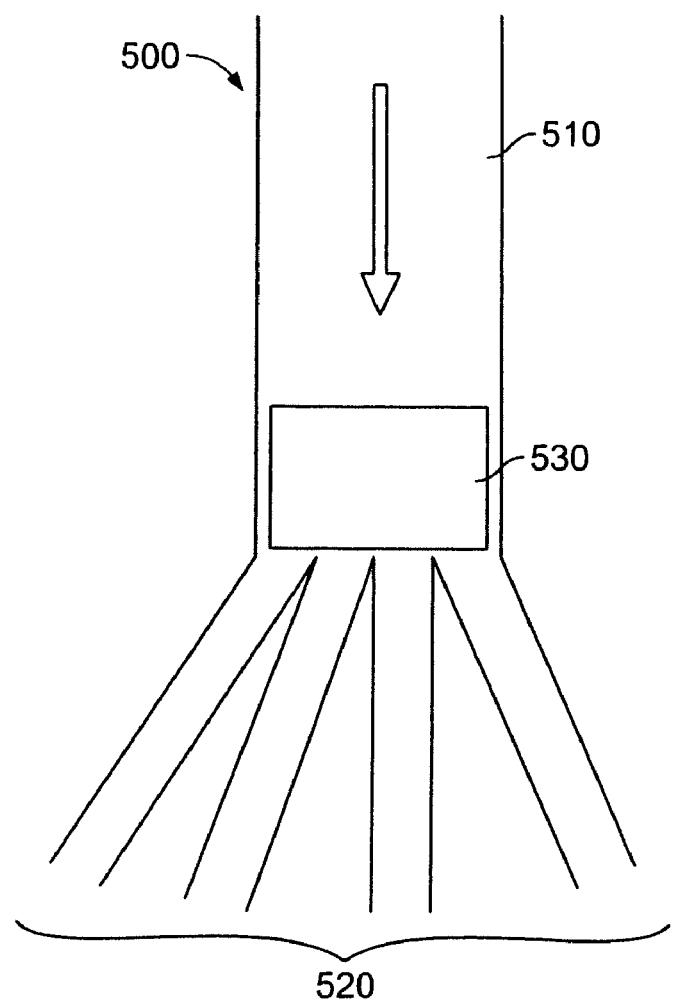
FIG. 6 shows an embodiment of the present invention in which mixing components of two or more input streams creates a single thoroughly mixed output streams.

One example of the invention is a variation of chromatography 500 in which a single input sample 510 is dispersed into several discrete fractions 520 as shown in FIG. 6, each of which can be collected separately. This can be accomplished most simply with a single array of tweezer 530 whose geometric distribution changes discretely or continuously as it crosses the interfaces between output streams.

Figure 7:
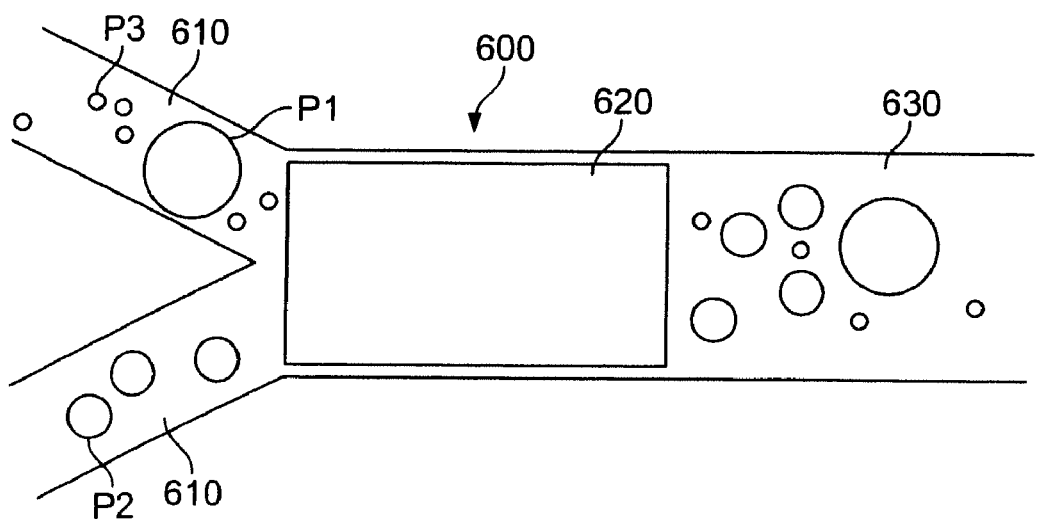
FIG. 7 is an illustration in which two or more input streams are mixed to create a single, thoroughly mixed, output stream.

Another example would be mixing the components of two or more input streams to create a single thoroughly mixed output streams. This is illustrated in FIG. 7. Particles of types P1, P2, and P3 from input streams 610 are mixed at an interaction region 620, where an array of optical traps is projected, to come out into a single output stream 630. Such mixing is difficult in microfluidic systems whose strength is their freedom from mixing. Operating optical fractionation in reverse provides a system for dynamically and selectively mixing samples in microfluidic systems.

Other examples arise from the combinatorial nature of the described switching and might include embodiments for drug testing in which microbes are transferred through streams of drug candidates and individually selected based on their responses. The benefit of this approach is that early-stage testing could proceed on vanishingly small samples by gauging their influence on individual microbes.

Other possible examples include selecting the precipitated products of reactions ongoing in the streams, for example to retain products of a certain size or with particular optical properties. These products then can be transferred into additional flows to facilitate multi-step reactions, fabricating core-shell nanoparticles providing one example. Because this process can proceed continuously, it may provide the basis for manufacturing such products in quantity. The benefit here over wet-chemistry methods is the generic ability to optimize the product without regard to chemical kinetics.

The present invention also involves a particular class of modifications to $\psi(r)$ that lead to a number of useful properties. In particular, this involves the class of modulated phase profiles, $$\phi(r) = \alpha_m \sin(m\theta - \theta_m) \quad (2)$$

where $\theta$ is the azimuthal angle around the optical axis, m is the index corresponding to an m-fold sinusoidal modulation, and $\alpha_m$ is the associated depth of modulation. The phase angle $\theta_m$ can be used to rotate the entire pattern relative to the reference direction. More general profiles can be constructed using Fourier's theorem:

$$\varphi(r) = \sum_{m=0}^{\infty} \alpha_m \sin(m\theta). \quad (3)$$

Eqs. (2) and (3) introduce controlled m-fold aberrations into the incident beam. The aberrations tend to blur the focus along selected directions, thereby extending the intensity distribution along those directions, and reducing the intensity gradients along those directions. This effect is shown in FIG. 1. The extension of the intensity distribution is useful for orienting extended objects. The reduction of the intensity gradients selectively weakens optical gradient force trapping along those directions.

When orienting extended objects, the phase structure from Eq. (3) is selected to fit the profile of the object to be oriented. Once projected, this pattern will tend to orient the extended object as desired.

For applications in optical fractionation, individual optical traps can be selectively weakened in desired directions. These directions may be aligned with the lattice directions of the array of traps, with the direction of the force-driving objects through the array or in some other direction. The modulation's profile and depth can be selected to optimize transport of selected objects through the array, particularly in cases where such leakage can improve the process' selectivity.

The profiles described by Eqs. (2) and (3) can be combined with other mode-forming and trap-generating phase functions to create other types of modulated optical traps and to place them selectively in three dimensions. The present invention separates the notion of modulating the intensity profile from the notion of generating helical modes of light, and thereby facilitates applications that do not rely on the properties of helical modes.

Implementing these and other applications of holographic optical traps requires accurate and efficient methods for computing the necessary phase patterns. According to scalar diffraction theory, the (complex) field $E(\vec{r})$ in the focal plane of a lens of focal length $f$ is related to the field, $u(\vec{\rho})\exp(i\phi(\vec{\rho}))$, in its input plane by a Fraunhofer transform, $$E(\vec{r}) = \int u(\vec{\rho})\exp(i\varphi(\vec{\rho}))\exp\left(-i\frac{k\vec{r}\cdot\vec{\rho}}{2f}\right)d^2\rho, \quad (4)$$

where $u(\vec{p})$ and $\phi(\vec{p})$ are the real-valued amplitude and phase, respectively, of the field at position F in the input pupil, and $k=2\pi/\lambda$ is the wave number of light of wavelength $\lambda$.

If $u(\vec{\rho})$ is the amplitude profile of the collimated laser used to power the optical trap array, then $\phi(\vec{\rho})$ is the kinoform encoding the pattern. Most practical DOEs, including those projected with SLMs, comprise an array $\vec{\rho}_j$ of discrete phase pixels, each of which can impose any of P possible discrete phase shifts $\phi_j \in \{0, \ldots, \phi_{P-1}\}$. The field in the focal plane due to such an N-pixel DOE is, therefore, $$E(\vec{r}) = \sum_{j=1}^{N} u_j \exp(i\varphi_j) T_j(\vec{r}), \quad (5)$$

where the transfer matrix describing the propagation of light from input plan to output plane is $$T_j(\vec{r}) = \exp\left(-i\frac{k\vec{r}\cdot\vec{\rho}}{2f}\right). \quad (6)$$

Unlike more general holograms, the desired field in the output plan of a holographic optical trapping system consists of M discrete bright spots located at $\vec{r}_m$:

$$E(\vec{r}) = \sum_{m=1}^{M} E_m(\vec{r}), \text{ with} \quad (7)$$

$$E_m(\vec{r}) = \alpha_m \delta(\vec{r} - \vec{r}_m) \exp(i\xi_m), \quad (8)$$

where $\alpha_m$ is the relative amplitude of the m-th trap, normalized by $\Sigma_{m=1}^{M}|\alpha_m|^2=1$, and $\xi_m$ is its (arbitrary) phase. Here, $\delta(\vec{r})$ represents the amplitude profile of the focused beam of light in the focal plane, which may be treated heuristically as a two-dimensional Dirac delta function. The design challenge is to solve Eqs. (5), (6) and (7) for the set of phase shifts $\xi_m$, yielding the desired amplitudes $\alpha_m$ at the correct locations $\vec{r}_m$ given $u_j$ and $T_j(\vec{\rho})$.

The Gerchberg-Saxton algorithm and its generalizations, such as the adaptive-additive algorithm, iteratively solve both the forward transform described by Eqs. (5) and (6), and also its inverse, taking care at each step to converge the calculated amplitudes at the output plane to the design amplitudes and to replace the back-projected amplitudes, $u_j$ at the input plane with the laser's actual amplitude profile. Appropriately updating the calculated input and output amplitudes at each cycle can cause the DOE phase $\phi_j$, to converge to an approximation to the ideal kinoform, with monotonic convergence possible for some variants. The forward and inverse transforms mapping the input and output planes to each other typically are performed by fast Fourier transform (FFT). Consequently, the output positions $\vec{r}_m$ also are explicitly quantized in units of the Nyquist spatial frequency. The output field is calculated not only at the intended positions of the traps, but also at the spaces between them. This is useful because the iterative algorithm not only maximizes the fraction of the input light diffracted into the desired locations, but also minimizes the intensity of stray light elsewhere.

FFT-based iterative algorithms have drawbacks for computing three-dimensional arrays of optical tweezers, or mixtures of more general types of traps. To see this, one notes how a beam-splitting DOE can be generalized to include wave front-shaping capabilities.

A diverging or converging beam at the input aperture comes to a focus and forms a trap downstream or upstream of the focal plane, respectively. Its wave front at the input plane is characterized by the parabolic phase profile $$\varphi_z(\vec{\rho}, z) = \frac{k\rho^2 z}{f^2}, \quad (9)$$

where z is the focal spot's displacement along the optical axis relative to the lens' focal plane. This phase profile can be used to move an optical trap relative to the focal plane even if the input beam is collimated by appropriately augmenting the transfer matrix:

$$T_j^z(\vec{r}) = T_j(\vec{r}) K_j^z(\vec{r}), \quad (10)$$

where the displacement kernel is $$K_j^z(\vec{r}) = \exp(i\phi_z(\vec{\rho}_j, z)), \quad (11)$$

and using the result as the kernel of Eq. (5).

Similarly, a conventional TEM beam can be converted into a helical mode by imposing the phase profile $$\phi_l(\vec{\rho}) = l\theta, \quad (12)$$

where $\theta$ is the azimuthal angle around the optical axis and l is an integral winding number known as the topological charge. Such corkscrew-like beams focus to ring-like optical traps known as optical vortices that can exert torques as well as forces. The topology-transforming kernel $K_j^l(\vec{r}) = \exp(i\phi_l(\vec{\rho}_j))$ can be composed with the transfer matrix in the same manner as the displacement-inducing $K_j^z(\vec{r})$. An additional kernel can be incorporated in the same manner to implement modulated tweezers according to Eq. (2).

A variety of comparable phase-based mode transformations have been described, each with applications to single-beam optical trapping. All can be implemented by augmenting the transfer matrix with an appropriate transformation kernel. Moreover, different transformation operations can be applied to each beam in a holographic trapping pattern independently, resulting in general three-dimensional configurations of diverse types of optical traps.

Calculating the phase pattern $\phi_j$ encoding multifunctional three-dimensional optical trapping patterns requires only a slight elaboration of the algorithms used to solve Eq. (5) for two-dimensional arrays of conventional optical tweezers. The primary requirement is to measure the actual intensity projected by $\phi_j$ into the m-th trap at its focus. If the associated diffraction-generated beam has a non-trivial wave front, then it need not create a bright spot at its focal point. On the other hand, if we assume that $\phi_j$ creates the required type of beam for the m-th trap through a phase modulation described by the transformation kernel $K_{j,m}(\vec{r})$, then applying the inverse operator, $K_{j,m}^{-1}(\vec{r})$ in Eq. (5) would restore the focal spot.

This principle was first applied to creating three dimensional trap arrays in which separate translation kernels were used to project each desired optical tweezer back to the focal plane as an intermediate step in each iterative refinement cycle. Computing the light projected into each plane of traps in this manner involves a separate Fourier transform for the entire plane. In addition to its computational complexity, this approach also requires accounting for out-of-focus beams propagating through each focal plane, or else suffers from inaccuracies due to failure to account for this light.

A substantially more efficient approach involves computing the field only at each intended trap location, as $$E_m(\vec{r}_m) = \sum_{j=1}^{N} K_{j,m}^{-1}(\vec{r}_m) T_j(\vec{r}_m) \exp(-i\varphi_j), \quad (13)$$

and comparing the resulting amplitude $\alpha_m = |E_m|$ with the design value. Unlike the FFT-based approach, this per-trap algorithm does not directly optimize the field in the inter-trap region. Conversely, there is no need to account for interplane propagation. If the values of $\alpha_m$ match the design values, then no light is left over to create ghost traps.

Iteratively improving the input and output amplitudes by adjusting the DOE phases, $\phi_j$, involves backtransforming from each updated $E_m$ using the forward transformation kernels, $K_{j,m}(\vec{r}_m)$ with one projection for each of the M traps. By contrast, the FFT-based approach involves one FFT for each wave front type within each plane and may not converge if multiple wave front, types are combined within a given plane. The only adjustable parameters in Eqs. (8) and (13) are the relative phases $\xi_m$ of the projected traps. These M−1 real-valued parameters must be adjusted to optimize the choice of discrete-valued phase shifts, $\phi_j$, subject to the constraint that the amplitude profile $u_j$ matches the input laser's. This problem is likely to be underspecified for both small numbers of traps and for highly complex heterogeneous trapping patterns. The result for such cases is likely to be optically inefficient holograms whose projected amplitudes differ from their ideal values.

Equation (13) suggests an alternative approach for computing DOE functions for discrete HOT patterns. The operator, $K_{j,m}^{-1}(\vec{r}_m)T_j(\vec{r}_m)$ describes how light in the mode of the m-th trap propagates from position $\vec{\rho}_j$ Fib on the DOE to the trap's projected position $\vec{r}_m$, in the lens' focal plane. If we were to change the DOE's phase $\phi_j$ at that point, then the superposition of rays composing the field at $\vec{r}_m$ would be affected. Each trap would be affected by this change through its own propagation equation. If the changes led to an overall improvement, then one would be inclined to keep the change, and seek other such improvements. If, instead, the result were less good, $\phi_j$ would be restored to its former value and the search for other improvements would continue. This is the basis for direct search algorithms, including the extensive category of simulated annealing and genetic algorithms. These related algorithms differ in their approach to accepting and rejecting candidate changes, and in their methods for creating such candidates. Here, it is described how to apply these algorithms specifically to HOT CGH computation.

In its most basic form, direct search involves selecting a pixel at random from a, trial phase pattern, changing its value to any of the P−1 alternatives, and computing the effect on the projected field. This operation can be performed efficiently by calculating only the changes at the M trap's positions due to the single changed phase pixel, rather than summing over all pixels. The updated trial amplitudes then are compared with their design values and the proposed change is accepted if the overall amplitude error is reduced. The process is repeated until the acceptance rate for proposed changes becomes sufficiently small.

The key to a successful and efficient direct search for $\phi_j$ is to select a function that effectively quantifies projection errors. The standard cost function, $\Sigma_{m=1}^{M}(I_m - \in I_m^{(D)})^2$, assesses the mean-squared deviations of the m-th trap's projected intensity $I$, from its design value $I_m^{(D)}$, assuming an overall diffraction efficiency of $\in$. It requires an accurate estimate for $\in$ and places no emphasis on uniformity in the projected traps' intensities. An alternative, $$C = -\langle I \rangle + f\sigma, \quad (14)$$

proposed by Meister and Winfield avoids both shortcomings. Here, $$\langle I \rangle = \frac{1}{M}\sum_{m=1}^{M} I_m$$

is the mean intensity at the traps and $$\sigma = \sqrt{\frac{1}{M}\sum_{m=1}^{M}(I_m - \gamma I_m^{(D)})^2} \quad (15)$$

measures the deviation from uniform convergence to the design intensities. Selecting $$\gamma = \frac{\sum_{m=1}^{M} I_m I_m^{(D)}}{\sum_{m=1}^{M} (I_m^{(D)})^2} \quad (16)$$

minimizes the total error and accounts for non-ideal diffraction efficiency. The weighting fraction $f$ sets the relative importance attached to overall diffraction efficiency and uniform convergence.

In the simplest direct search for an optimal phase distribution, any candidate change that reduces C is accepted, and all others are rejected. Selecting pixels to change at random reduces the chances of the search becoming trapped by suboptimal configurations that happen to be highly correlated. The typical number of trials required for practical convergence should scale as N P, the product of the number of phase pixels and the number of possible phase values. In practice, this rough estimate is accurate if P and N are comparatively small. For larger values, however, convergence is attained far more rapidly, often within N trials, even for fairly complex trapping patterns.

Figure 2:
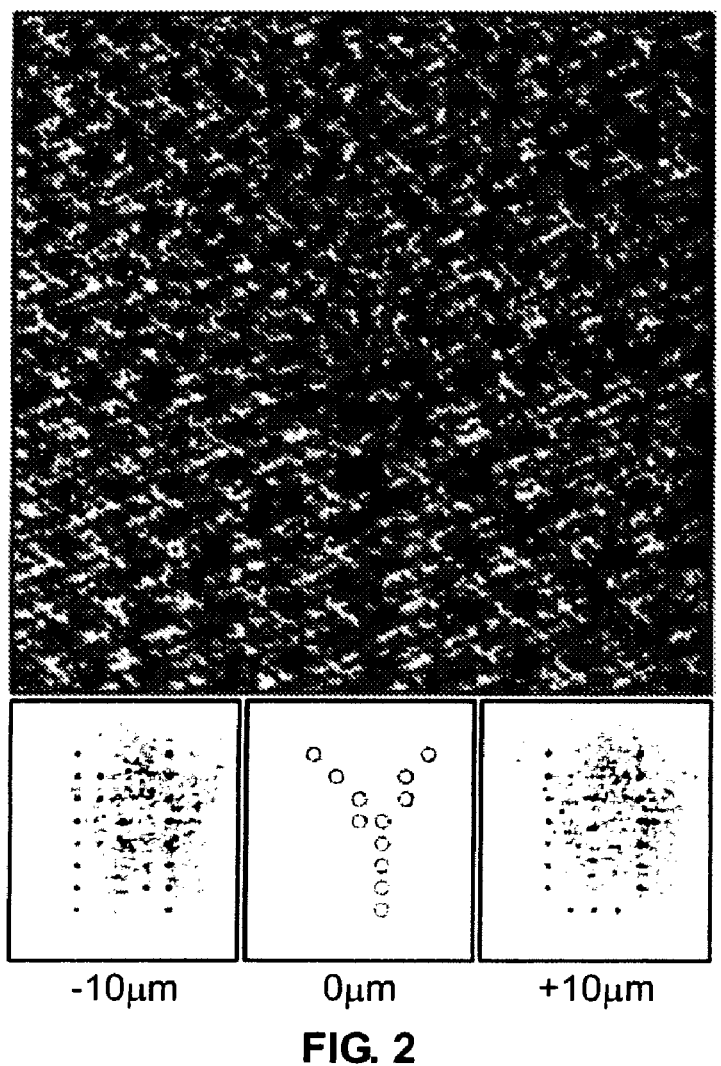
FIG. 2 shows a three-dimensional multifunctional holographic optical trap array created with a single phase-only DOE computed with the direct search algorithm, wherein the top DOE phase pattern includes white regions corresponding to a phase shift of $2\pi$ radians and black regions corresponding to 0, and wherein the bottom projected optical trap array is shown at $z=-10$ μm, 0 μm and $+10$ μm from the focal plane of a 100×, NA 1.4 objective lens, with the traps being spaced by 1.2 μm in the plane, and the 12 traps in the middle plane consisting of $l=8$ optical vortices.

FIG. 2 shows a typical application of the direct search algorithm to computing a HOT DOE consisting of 51 traps, including 12 optical vortices of topological charge l=8, arrayed in three planes relative to the focal plane. The 480× 480 pixel phase pattern was refined from an initially random superposition of fields in which amplitude variations were simply ignored. The results in FIG. 2 were obtained with a single pass through the array. The resulting traps, shown in the bottom three images, appear uniform. This effect was achieved by setting the optical vortices' brightness to 15 times that of the conventional optical tweezers. This single hologram therefore demonstrates independent control over three-dimensional position, wave front topology, and brightness of all the traps.

To demonstrate these phenomena more quantitatively, standard figures of merit are augmented with those known in the art. In particular, the DOE's theoretical diffraction efficiency is commonly defined as $$Q = \frac{1}{M}\sum_{m=1}^{M}\frac{I_m}{I_m^{(D)}}, \quad (17)$$

and its root-mean-square (RMS) error as $$e_{rms} = \frac{\sigma}{\max(I_m)}. \quad (18)$$

The resulting pattern's departure from uniformity is usefully gauged as $$u = \frac{\max(I_m/I_m^{(D)} - \min(I_m/I_m^{(D)}))}{\max(I_m/I_m^{(D)} + \min(I_m/I_m^{(D)}))}. \quad (19)$$

Figure 3:
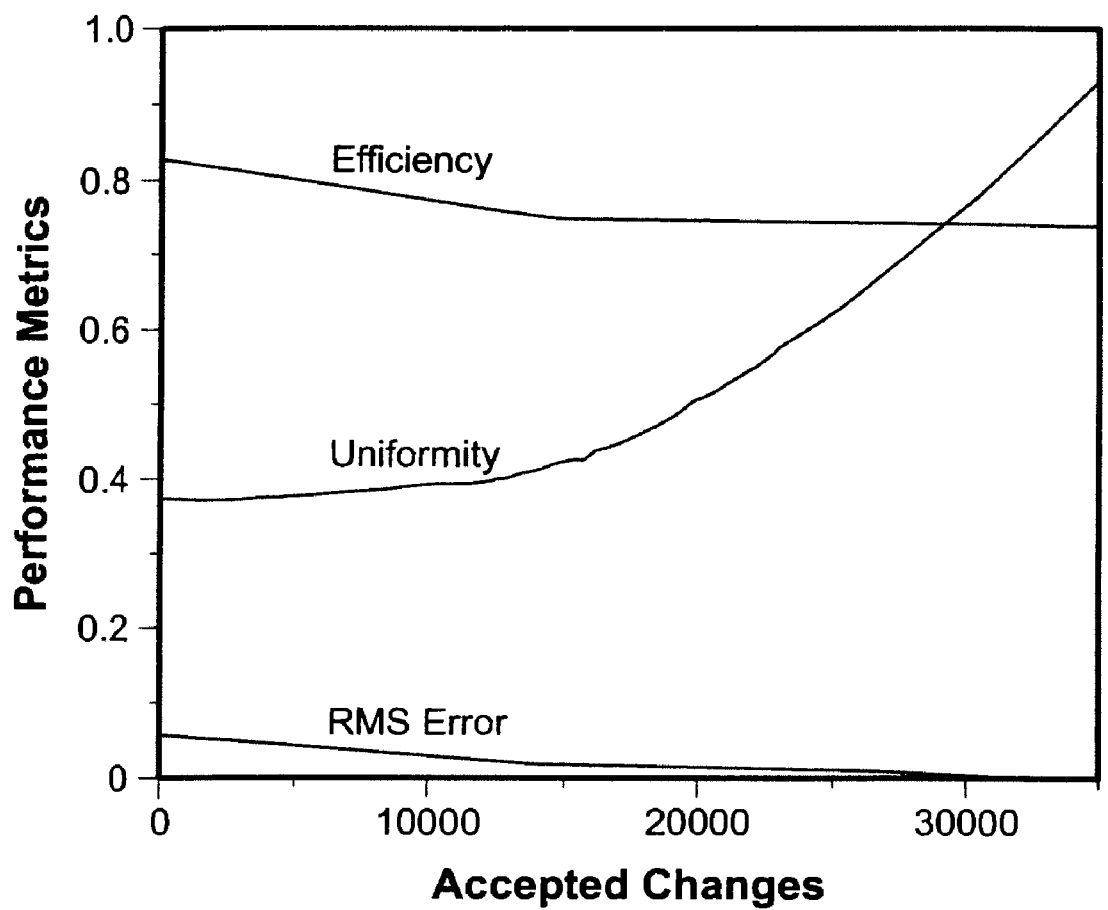
FIG. 3 is a plot showing performance metrics for the algorithm that calculated the hologram in FIG. 2 as a function of the number of accepted single-pixel changes.

These performance metrics are plotted in FIG. 3 as a function of the number of accepted single-pixel changes. The overall acceptance rate for changes after a single pass through the entire DOE array was better than 16%.

FIG. 3 demonstrates that the direct search algorithm trades off a small percentage of the overall diffraction efficiency in favor of substantially improved uniformity.

Two-dimensional phase holograms contain precisely enough information to encode any two-dimensional intensity distribution. A three-dimensional or multi-mode pattern, however, may require both the amplitude and the phase to be specified in the lens' focal plane. In such cases, a two-dimensional phase hologram can provide at best an approximation to the desired distribution of traps.

The most straightforward elaboration of a direct search is the class of simulated annealing algorithms. Like direct search, simulated annealing repeatedly attempts random changes to randomly selected pixels. Also like direct search, a candidate change is accepted if it would reduce the cost function. Simulated annealing avoids becoming trapped away from the globally optimal solution by also accepting some changes that increase the cost function, with a probability P that falls off exponentially with the increase ΔC in cost:

$$P = \exp\left(-\frac{\Delta C}{C_0}\right). \quad (20)$$

In this case, $C_0$ is a characteristic cost that plays the role of the temperature in the standard Metropolis algorithm used in Monte Carlo simulations. Increasing $C_0$ results in an increased acceptance rate of costly changes. This has the benefit of kicking the phase pattern out of any local minima so that the globally optimal solution may be found. The increased acceptance rate also increases the time required to converge to that solution, however, and therefore increases the computational cost of the calculation.

The tradeoff between exhaustive and efficient searching can be optimized by selecting an appropriate value of $C_0$. Unfortunately, the best choice may be different for each application. Starting $C_0$ at a large value that promotes exploration and then reducing it to a lower value that speeds convergence offers a convenient compromise.

Effective searches may be implemented by attempting to change multiple pixels simultaneously, instead of one at a time. Different patterns of multi-pixel changes may be particularly effective for optimizing trap-forming phase holograms of different types, and the approaches used to identify and improve such patterns generally are known as genetic algorithms.

All of these more sophisticated approaches may have applications in designing high-efficiency, high-accuracy DOEs for HOT applications. In many cases of practical interest, the simplest is also the fastest and offers substantial advantages over previously reported algorithms.

Figure 8:
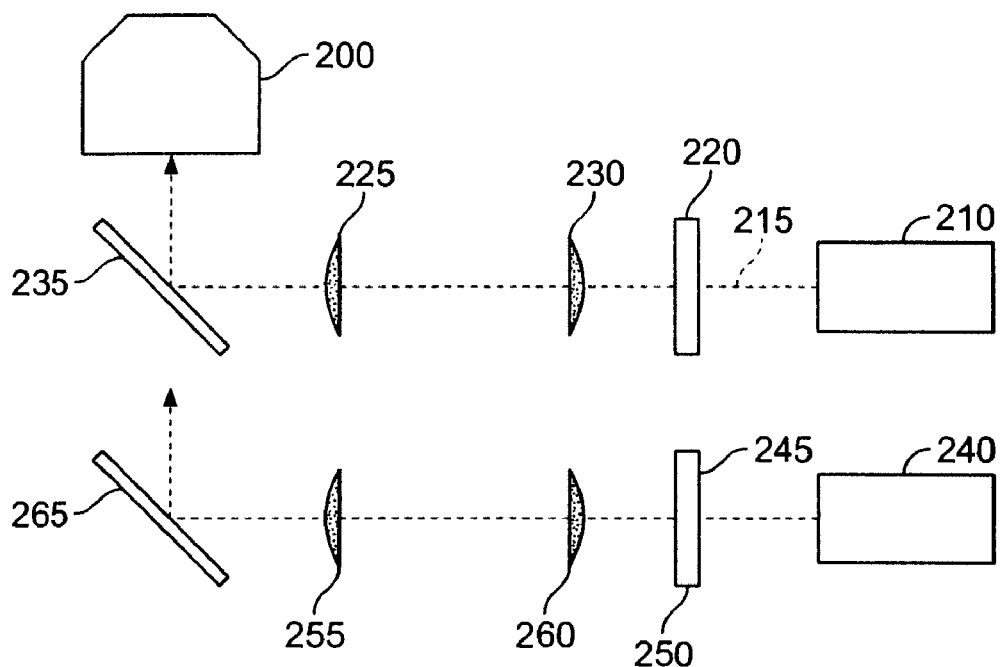
FIG. 8 is a representation of one method for creating two-color holographic optical traps according to one embodiment of the present invention.

FIG. 8 shows a first implementation of two-color holographic optical traps (2C-HOT). In FIG. 8, an objective lens 200 is used to focus light from laser 210 and laser 240 into optical traps, which are intended to be projected into a sample. For the first the path of laser beam 215 emanating from laser 210, the wavefronts of this beam are modulated by the diffractive optical element (DOE) 220 before being projected by lenses 225 and 230 to the input plane of objective 200. Lenses 225 and 230 should be understood to be any relay optical train accomplishing the transfer of the modulated beam 215 to the focusing element 200. On its way to the focusing element 200, beam 215 is redirected by reflection off of an element 235, which is either a dichroic mirror, a partially silvered mirror, a polarization-selective beam splitter, or the like. For purposes of this application, this element, or any equivalent element is considered to be a dichroic mirror. The element 235 is designed to reflect the laser beam 215 and to transmit other light, either as a function of its wavelength, its polarization, or some other properties.

The ability of the element 235 to reflect the HOT-forming laser beam 215 while transmitting other light provides the system with the capability to form images of the sample being manipulated, the imaging light being able to pass through the element 235 to a conventional imaging train. It also provides a method for implementing 2C-HOT.

In the scenario shown in FIG. 8, a second laser 240 projects a second laser beam 245, which is operated on by DOE 250. This modified beam 245 is relayed by lenses 255 and 260 to the objective 200, and thereby forms holographic optical traps. This second beam 245 is reflected into the input aperture of the objective 200 by a dichroic 265. This element is designed to reflect laser light 245 from the laser 240, and may optionally transmit other light. The dichroic 235, by contrast, is designed to transmit this light so that it can reach the objective 200 and be focused into traps.

It should be emphasized that the beams 215 and 245 need not be generated by separate lasers, but instead could be created by a single laser beam that has been split and operated on by other elements, not shown. Also, the DOE's are shown operating in transmission. They might equivalently be replaced by reflective DOE's with the necessary modifications to the optical trains. The DOE's can modulate the phase, amplitude, and polarization of the incident beams in any way required to create holographic optical traps, and can include computer-addressed spatial light modulators.

Figure 9:
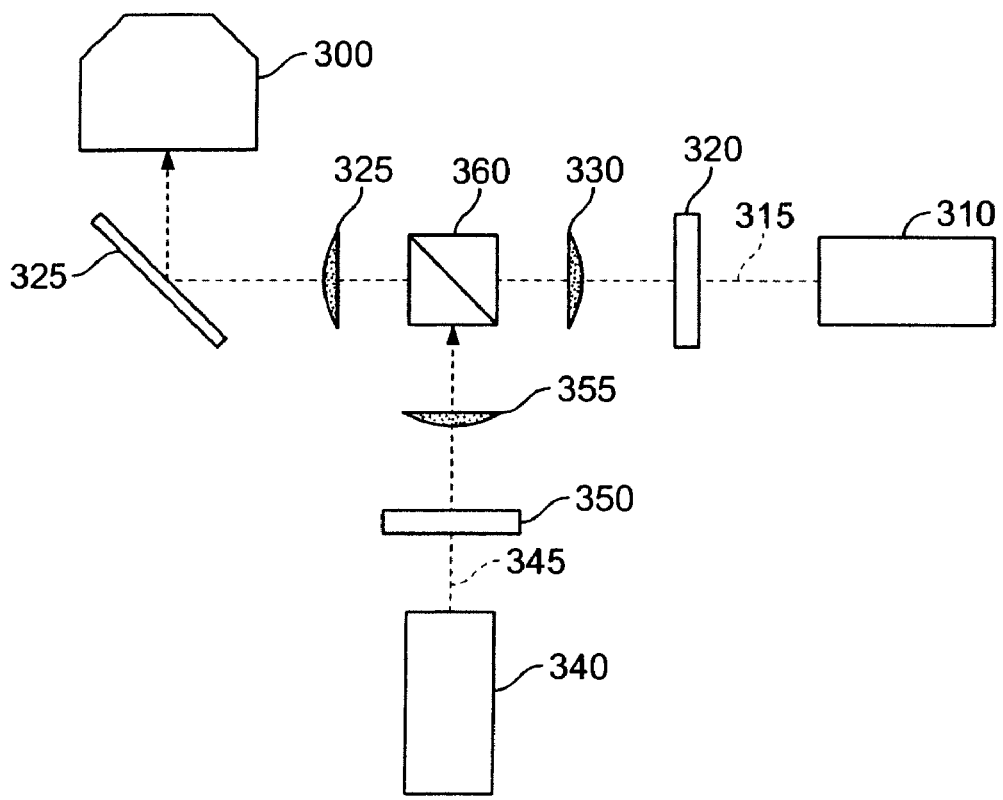
FIG. 9 is a representation of a second method for creating two-color holographic optical traps according to one embodiment of the present invention.

FIG. 9 is a representation of a variant of the design of FIG. 8. In FIG. 9, a laser 310 provides a first beam 315, which is operated on by a first DOE 320 before being relayed by first and second lenses 325 and 330 to a focusing element 300 to form optical traps. A first dichroic 320 is designed to reflect this trapping light into the focusing element, and optionally to transmit other light. The first beam 315 passes through a beam splitter 360, which also could be a dichroic mirror, a polarization-selective beam splitter or a partially silvered mirror, for example.

The beam splitter 360 is designed to reflect a second beam 345 produced by a second laser 340. The second beam 345 is operated on by a second DOE 350 to form a second set of holographic optical traps. The modulated light is relayed to focusing the focusing element 300 by the combination of the first lens 325 and a third lens 355, the beam splitter 360, and a second dichroic 350. Unlike the previous method, the second dichroic 350 is designed also to reflect light 345 from the laser 340.

The first and second beams, 315 and 345 travel along the same optical axis downstream of the beam splitter 360.

Figure 10:
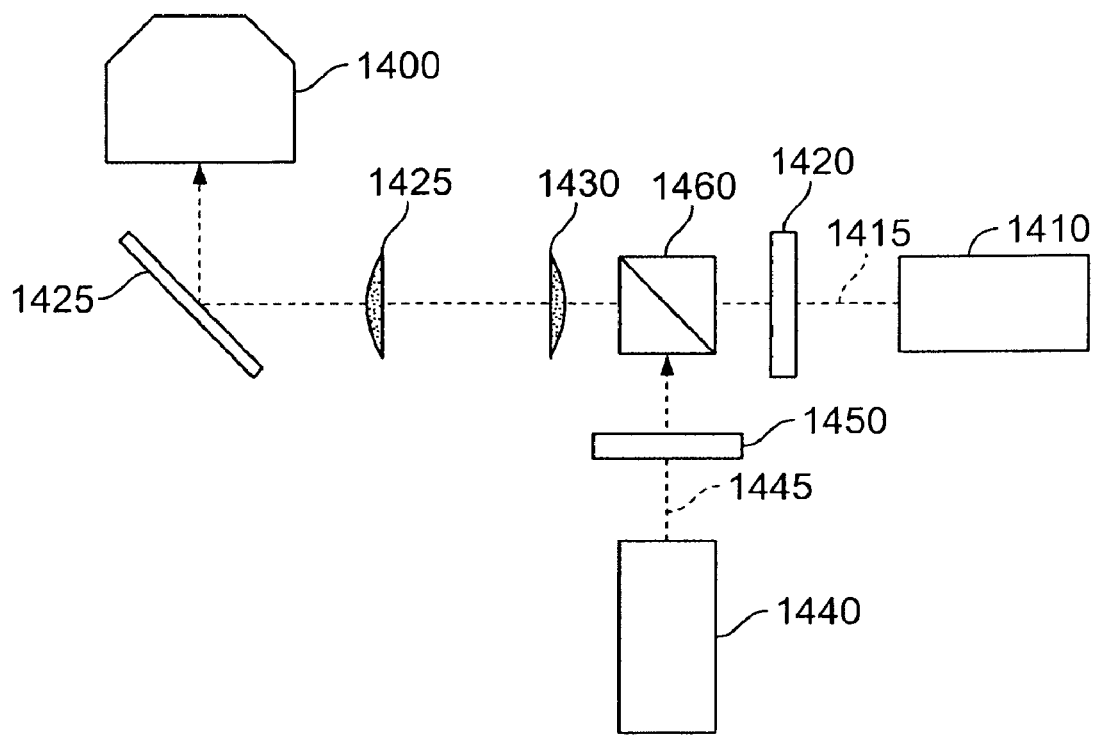
FIG. 10 is a representation of a third method for creating two-color holographic optical traps according to one embodiment of the present invention.

FIG. 10 shows still another variation of the present invention. In this case, first and second beams 1415 and 1445 from first and second lasers 1410 and 1440 are focused into traps by focusing an element 1400 after being relayed by first and second lenses 1425 and 1430 and being reflected by a dichroic 1435. The two beams are separately operated on by first and second DOE's 1420 and 1450, as shown. Once modulated by the first DOE 1420, the first beam 1415 passes through a beam splitter 1460, whereas the second beam 1445 is reflected by the beam splitter 1460 after being operated on by the second DOE 1450. As in the system of FIG. 9, the dichroic 1425 is designed to reflect both the first and second beams 1415 and 1445 and may transmit other light.

Figure 11:
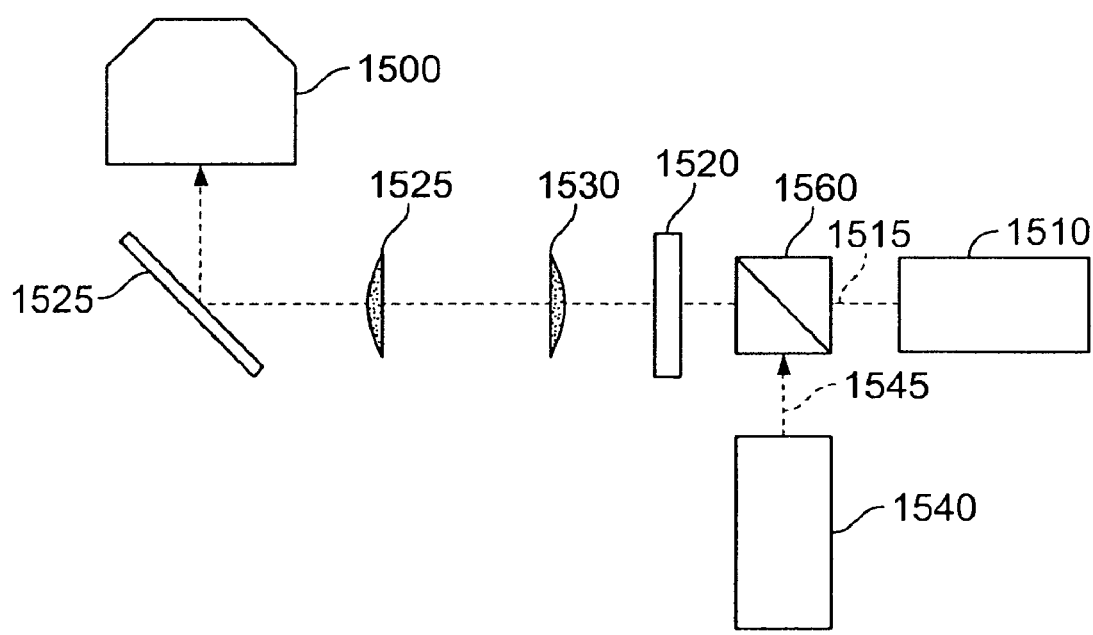
FIG. 11 is a representation of a fourth method for creating two-color holographic optical traps according to one embodiment of the present invention.

FIG. 11 shows an optical train according to yet another embodiment of the present invention. In this embodiment, first and second laser beams 1515 and 1545 produced by first and second lasers 1510 and 1540 are directed onto the same optical axis by a beam splitter 1560 and are operated on by the same DOE 1520. The two modulated beams then are relayed by first and second lenses 1525 and 1530 to a focusing element 1500, after being reflected by a dichroic 1525. In the case that the first and second beams 1515 and 1545 have different wavelengths, this two-color DOE can imprint a different phase modulation on each, resulting in two distinct patterns of traps being projected. This DOE must be calculated specifically to accommodate two distinct beams and, therefore, has additional design considerations when compared with the single-wavelength DOE's described in the previous methods.

Figure 13:
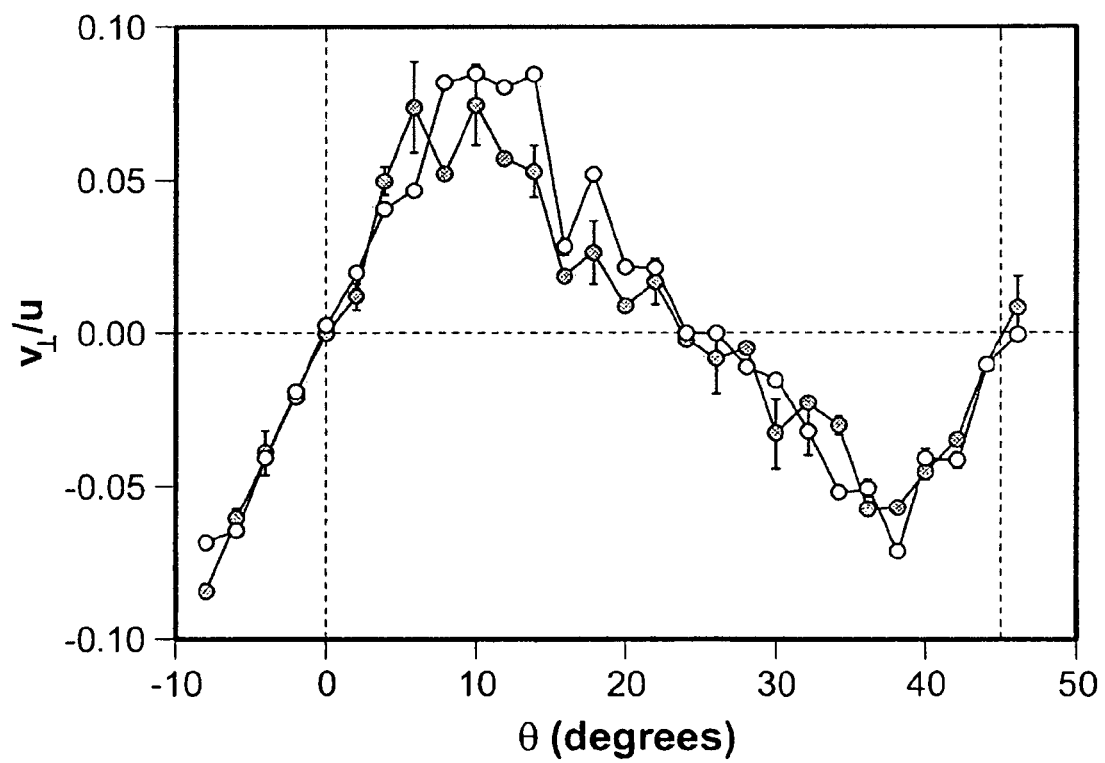
FIG. 13 is a plot showing the transverse velocity $v_\perp$ relative to flow speed $v$, of 1.5 μm diameter silica spheres dispersed in water, as a function of an orientation angle $\Theta$ of a 10×10 array of holographic optical tweezers, wherein the two data sets shown were obtained for different values of the flow speed u.

In some applications, tuning fractionation by visual inspection may be undesirable or impractical. In such instances, an alternative characterization method based upon electrical (rather than optical) measurements may be preferable. FIG. 13 schematically depicts a representative implementation 1600 of optoelectrokinetic potentiometry. The sample consists of charged objects such as colloidal particles, macroions, or biological cells, which are dispersed in a solvent such as water. The sample flows at speed v, along a channel and through the gap between two electrodes. No potential will develop across this gap if the electrodes are arranged transverse to the flow direction, and an electrometer connected across the electrodes will register no voltage. This is the null condition for this measurement.

A measurement is performed by projecting an array of optical traps 1630 into the interelectrode gap. These optical traps 1630 may be created, for example, with a holographic optical tweezer technique, with the generalized phase contrast method, or with an interferometrically generated optical lattice. Fluid-borne objects experience a structured potential energy landscape due to their interaction with the optical intensity distribution. Depending on their optical properties, they may be attracted to or repelled by the brightest regions. The following considerations apply to either case.

Particles are able to traverse an array of optical traps 1630 if the viscous drag force due to the flowing fluid exceeds the traps' 1630 maximum trapping force. Their trajectories nevertheless are influenced by encounters with these potential wells. If the trap array 1630 is aligned with the driving force, then particles simply hop from well to well along the line, their trajectories somewhat slowed. If, on the other hand, the trap array 1630, is inclined with respect to the flow direction, then particles can become locked into symmetry-selected directions through the potential energy landscape and thus can be deflected away from the direction of the driving force. This is the principle behind optical fractionation as discussed above.

One effect of this deflection is the creation of a component of the charged particles' velocity directed across the interelectrode gap. This optically-induced transverse speed, $v_\perp$, leads to a measurable electrokinetic potential whose magnitude depends on the transverse flow speed, the charge on the particles, and the particles' hydrodynamic properties. The relationship between $v_\perp$ and the measured voltage depends on properties of the particles and their solvent. The sign of the voltage depends on the sign of the particles' charge and the sign of $v_\perp$. The magnitude and direction of the transverse velocity depends, in turn, on details of the particles' interaction with the optical intensity pattern, and on the pattern's geometry. This means that the transverse voltage measured in this apparatus is sensitive to a wide range of properties in both the particles and their supporting electrolyte. One can also apply an external bias force 1605 to the sample 1610 which is a plurality of charged particles, orienting an array of the optical traps 1630 at a plurality of angles with respect to the bias force 1605 and then measuring the transverse voltage at each of the plurality of angles wherein each measurement of the transverse voltage is associated with a corresponding angle of the array at which the measurement is made.

Figure 12:
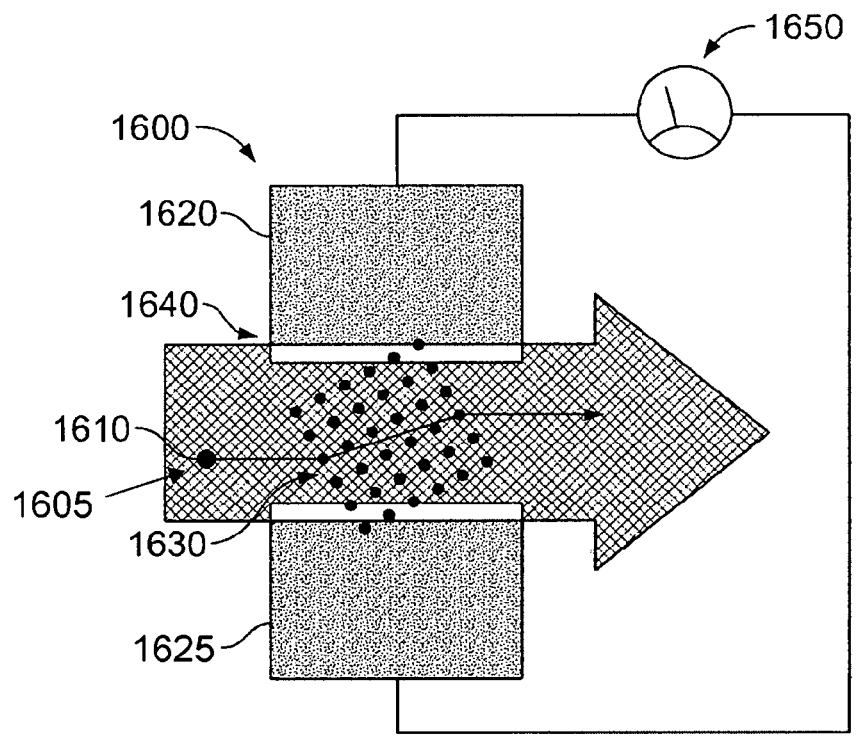
FIG. 12 is a schematic diagram of a practical implementation of optoelectrokinetic potentiometry.

FIG. 13 shows representative experimental data obtained for colloidal silica spheres. This plot shows the transverse velocity $v_\perp$ relative to flow speed v of 1.5 µm diameter silica spheres dispersed in water, as a function of orientation angle Θ of a 10×10 array of holographic optical tweezers. The transverse component of the particles' velocity increases as the array's orientation increases from Θ=0 (aligned) because particles remain locked in to the [1,0] lattice direction. Once the particles become unlocked from this commensurate path through the trap array, the deflection angle decreases and actually changes sign as the trajectories become locked in to the diagonal [1,1] direction. The transverse voltage measured in the apparatus of FIG. 12 would track this trend, including the sign reversal.

Given this information obtained over a range of orientations, the sign of the measured transverse potential indicates the sign of the flowing particles' charges. The angle and magnitude of maximum and minimum transverse voltage can be used to gauge the magnitude of the particles' charges. Their dependence on laser power and the array's lattice constant can be used to measure the particles' hydrodynamic radius and the polydispersity in size.

Even a single measurement at fixed orientation can provide information on the sign of the transported particles' charge. A rapid series of measurements as a function of orientation, laser power, flow speed, trap geometry, or any combination of these can be used to extract very detailed information about a spectrum of properties. This approach, therefore, provides more information about a wider range of properties than any other single measurement technique. The measurement is easily automated, and could be useful in process control and quality assurance applications. It operates naturally on continuous streams, as well as on discrete batches, and so could be integrated into manufacturing processes.

Electrokinetically assaying of the state of kinetically locked in transport also can be used to optimize optical fractionation of charged species without directly imaging the flowing sample or sampling the downstream fractions. Consequently, the present invention also provides substantial benefits for automated optical fractionation.

While several embodiments have been shown and described herein, it should be understood that changes and modifications can be made to the invention without departing from the invention in its broader aspects. Various features of the invention are defined in the following Claims.

What is claimed is:

1. A method for characterizing a charged solute, comprising the steps of:
 operatively spacing apart a first electrode and a second electrode to form an interelectrode gap;

providing an electrometer in communication with the first electrode and the second electrode;

projecting an array of optical traps positioned in the inter-electrode gap;

using the first electrode and second electrode to measure the transverse electrokinetic voltage arising from the deflection of the charged solute by the array of optical traps as the charged solute is being driven by solvent flow through the array of optical traps; and using the transverse electrokinetic voltage to characterize the charged solute.

2. In the method of claim 1 wherein an external biasing force is present, the improvement, comprising the steps of:

applying the external biasing force to a plurality of charged particles;

orienting the array at a plurality of angles with respect to the biasing force; and measuring the transverse electrokinetic voltage at each of the plurality of angles, wherein each measurement of the transverse electrokinetic voltage is associated with a corresponding angle of the array at which the measurement is made.

3. The method of claim 2, further comprising the step of determining a maximum transverse electrokinetic voltage, a minimum transverse electrokinetic voltage and the corresponding angles of the array.

4. The method of claim 3, further comprising the step of calculating the magnitude of the charged particles' charge from the maximum transverse electrokinetic voltage, the minimum transverse electrokinetic voltage, and the respective corresponding angles of the array.

5. The method as defined in claim 1 further comprising the step of determining magnitude of charge of the solute from the transverse electrokinetic voltage.

6. The method as defined in claim 5 wherein the step of determining magnitude of charge comprises measuring magnitude of maximum and minimum values of the transverse electrokinetic voltage.

7. The method as defined in claim 1 further comprising the step of determining a particle hydrodynamic radius for the solute from the transverse electrokinetic voltage.

8. The method as defined in claim 7 wherein a laser is used to form the array of optical traps and the step of determining a particle hydrodynamic radius comprises measuring dependence of the transverse electrokinetic voltage on power from the laser used to form the array of optical traps.

9. The method as defined in claim 7 wherein the step of determining a particle hydrodynamic radius comprises measuring a lattice constant of the array of optical traps.

10. The method as defined in claim 1 further including the step of measuring sign of charge for the charted solute by determining sign of the transverse electrokinetic voltage.

11. The method as defined in claim 1 further including the step of determining polydispersity in size of particles of the charged solute by measuring at least one of maximum transverse electrokinetic voltage, minimum transverse electrokinetic voltage, dependence of the maximum transverse electrokinetic voltage and the minimum transverse electrokinetic voltage on power of a laser used to form the optical traps and dependence of the maximum transverse electrokinetic voltage and minimum transverse electrokinetic voltage on lattice constant of the array of optical traps.

12. The method as defined in claim 1 further including the step of determining flow velocity of the charged solute from measured values of transverse velocity of the charged solute.

13. The method as defined in claim 1 further including the step of measuring as a function of angular orientation at least one of power of a laser used to form the optical traps, flow speed of the charged solute, optical trap geometry and combinations thereof to obtain detailed information about properties of the charged solute.

* * * * *